(12) United States Patent
Lathers et al.

(10) Patent No.: US 11,904,087 B2
(45) Date of Patent: Feb. 20, 2024

(54) PASSIVE SURGICAL ACCESS PORT FILTRATION FITTINGS

(71) Applicant: Conmed Corporation, Utica, NY (US)

(72) Inventors: Steven Lathers, Littleton, CO (US); Mahesh Krishnamoorthy, Parker, CO (US)

(73) Assignee: Conmed Corporation, Largo, FL (US)

( * ) Notice: Subject to any disclaimer, the term of this patent is extended or adjusted under 35 U.S.C. 154(b) by 274 days.

(21) Appl. No.: 17/237,700

(22) Filed: Apr. 22, 2021

(65) Prior Publication Data

US 2022/0257877 A1 Aug. 18, 2022

Related U.S. Application Data

(60) Provisional application No. 63/150,457, filed on Feb. 17, 2021.

(51) Int. Cl.
*A61B 17/34* (2006.01)
*A61M 13/00* (2006.01)

(52) U.S. Cl.
CPC ....... *A61M 13/003* (2013.01); *A61B 17/3423* (2013.01); *A61B 2017/3419* (2013.01); *A61B 2217/005* (2013.01); *A61M 2205/75* (2013.01)

(58) Field of Classification Search
CPC ............ A61B 17/3421; A61B 17/3423; A61B 17/0218; A61M 13/003
See application file for complete search history.

(56) References Cited

U.S. PATENT DOCUMENTS 5,722,962 A * 3/1998 Garcia ................. A61M 1/784
604/264
6,685,665 B2 2/2004 Booth et al.
(Continued)

FOREIGN PATENT DOCUMENTS

CN 211433579 U 9/2020
KR 101704903 B1 2/2017
(Continued)

OTHER PUBLICATIONS

PCT International Search Report and Written Opinion dated Jun. 7, 2022, issued during the prosecution of PCT International Patent Application No. PCT/US2022/016467.
(Continued)

*Primary Examiner* — Si Ming Ku
(74) *Attorney, Agent, or Firm* — Locke Lord LLP; Scott D. Wofsy

(57) ABSTRACT

A trocar assembly includes a trocar including an elongated tubular member extending between a distal end configured to be inserted into a surgical site and a proximal portion including a trocar housing configured for introduction of surgical instruments into the tubular member, wherein the trocar housing includes at least one latch receptacle. The assembly includes a cap, wherein the housing of the cap is attached to the proximal portion of a trocar. The cap includes a housing configured to be removably attached to a proximal portion of a trocar. The housing includes a flow passage therethrough from a distal end of the housing to a proximal opening of the housing. A filter medium is included within the housing spanning the flow passage for filtration of flow through the flow passage.

15 Claims, 9 Drawing Sheets

(56) References Cited

U.S. PATENT DOCUMENTS

| | | |
|---|---|---|
| 10,492,827 B1 | 12/2019 | Velez-Cruz |
| 2009/0137943 A1 | 5/2009 | Stearns et al. |
| 2012/0283518 A1 | 11/2012 | Hart |
| 2018/0228510 A1* | 8/2018 | Holsten .............. B01D 46/0097 |
| 2019/0388631 A1 | 12/2019 | Silver et al. |
| 2021/0267639 A1 | 9/2021 | Fischer et al. |

FOREIGN PATENT DOCUMENTS

| | | |
|---|---|---|
| WO | 2020036497 A1 | 2/2020 |
| WO | 2021191885 A2 | 9/2021 |

OTHER PUBLICATIONS

PCT International Search Report and Written Opinon dated May 31, 2022, issued during the prosecution of PCT International Patent Application No. PCT/US2022/016470.

* cited by examiner

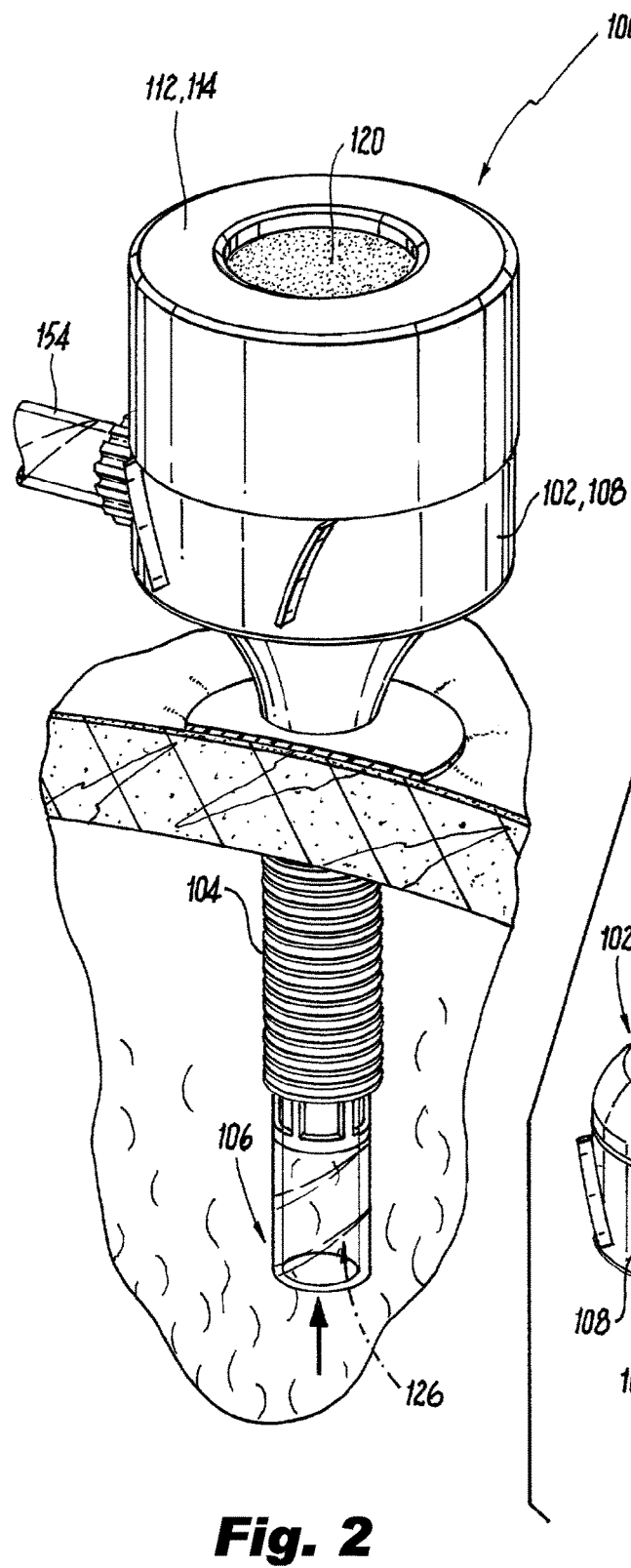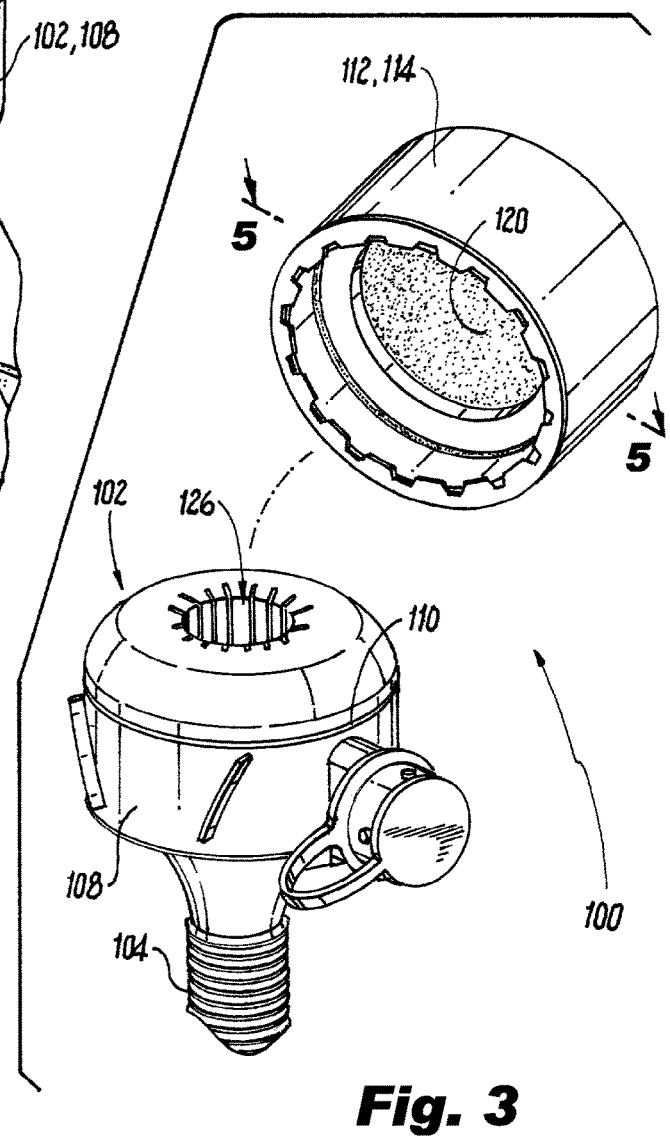
*Fig. 2*
*Fig. 3*

PASSIVE SURGICAL ACCESS PORT FILTRATION FITTINGS

CROSS-REFERENCE TO RELATED APPLICATIONS

This application claims priority to U.S. Provisional Patent Application No. 63/150,457, filed Feb. 17, 2021, which is incorporated by reference herein in its entirety.

BACKGROUND

1. Field

The present disclosure relates to passive filtration, and more particularly to passive filtration for surgical access ports such as used with insufflation systems.

2. Description of Related Art

Some surgical access ports are designed as open, valveless trocars with gas pressure barriers to prevent the loss of pneumoperitoneum. AirSeal® Access Ports as part of AirSeal® iFS insufflation management systems available from ConMed Corporation of Utica, New York can be introduced to a patient's surgical site during an insufflation procedure. Sometimes surgeons use AirSeal® iFS insufflation management systems in procedures where the AirSeal® Access Port is not used for access to the surgical site, e.g. when no surgical instruments are inserted through the trocar of the AirSeal® Access Port during in the procedure. In this scenario, the AirSeal® iFS insufflation management system provides the insufflation for the procedure. The AirSeal® System provides for stable pneumoperitoneum, and can also provide for smoke evacuation.

Regardless of the type of surgical access port used, due to the open nature of some access port designs, when there is no instrument passing through an access port there is an opportunity for particles to be emitted from inside a patient, through the access port opening, and into the operating room air. This can allow for unwanted or harmful particles to move from the intraabdominal cavity or other surgical site to the operating room where surgical staff/employees are present. This could include gasses or even pathogens that are harmful to the surgical staff/employees, who would have to rely on their PPE (personal protective equipment) for protection.

The conventional techniques have been considered satisfactory for their intended purpose. However, there is an ever present need for improved systems and methods for preventing unwanted or harmful particles from entering the operating room air through surgical access ports. This disclosure provides a solution for this need.

SUMMARY

A cap for a trocar assembly includes a housing configured to be removably attached to a proximal portion of a trocar. The housing includes a flow passage therethrough from a distal end of the housing to a proximal opening of the housing. A filter medium is included within the housing spanning the flow passage for filtration of flow through the flow passage.

A seal can extend circumferentially around the flow passage. The seal can be configured to engage the proximal portion of the trocar to drive all flow into and out of a main lumen of the trocar through the flow passage. A seal seat can be defined in the flow passage of the housing. The seal can be seated in the seal seat.

The filter medium can be an ultra-low particulate air (ULPA) filter medium. A first rim can be defined in the housing about the proximal opening and a second rim axially spaced apart from the first rim can be positioned within the flow passage. The second rim can be defined about an intermediate opening of the flow passage. The filter medium can be seated in a cavity of the housing axially between the first and second rims. The filter medium can have a larger outer perimeter defined in a circumferential direction than either of the proximal and intermediate openings so that flow through the flow passage must pass through the filter medium. The filter medium can fill the cavity. A seal seat can be defined in the flow passage of the housing, in a distal side of the second rim, wherein the seal can be seated in the seal seat. The distal side of the second rim can be angled conically to converge in a proximal direction. The distal end of the housing can include at least one inward extending latch member configured to engage a respective rim or detent of the trocar to maintain engagement of the housing to the trocar. The distal end of the housing can include a plurality of circumferentially spaced apart, inward extending latch members configured to engage a respective rim or detent of the trocar to maintain engagement of the housing to the trocar.

The distal end of the housing can include a passive opening connected to a first end of a tube. The second end of the tube can be connected to an access port fitting configured to engage to the proximal portion of the trocar for passive fluid communication through the flow passage, tube, access port fitting, and trocar.

The access port fitting can define a first opening therethrough generally aligned for passage of a surgical instrument therethrough and into a main lumen of the trocar, and a second opening lateral relative to the first opening, wherein the tube connects to the access port fitting at the second opening. The second opening can be larger than the first opening to direct outflowing gases preferentially through the second opening for filtering in the filter medium.

A trocar assembly includes a trocar including an elongated tubular member extending between a distal end configured to be inserted into a surgical site and a proximal portion including a trocar housing configured for introduction of surgical instruments into the tubular member, wherein the trocar housing includes at least one latch receptacle. The assembly includes a cap as described above, wherein the housing of the cap is attached to the proximal portion of a trocar.

A kit includes a trocar including an elongated tubular member extending between a distal end configured to be inserted into a surgical site and a proximal portion including a trocar housing configured for introduction of surgical instruments into the tubular member. The trocar housing includes at least one latch receptacle. The kit also includes a cap as described above.

A method includes regulating insufflation of a surgical site with a trocar introduced into the surgical site and venting fluid out of the surgical site through the trocar into a space external of the surgical site. The method includes capturing liquid droplets, solid particulate, and/or gas from the fluid in a filter medium in a flow path between the surgical site and the space external of the surgical site.

The filter medium can be external of any fluid circuit connecting between the trocar and an insufflator regulating insufflation with the trocar. The method can include accessing the surgical site through second access port. Accessing the surgical site through the second access port can include accessing the surgical site without accessing the surgical site through the first access port. It is also contemplated that the method can include accessing the surgical site through the trocar and diverting outflowing gas from the trocar though a lateral opening in a passive filtration cap on the trocar. The method can include evacuating smoke from the surgical site through the trocar. The method can include regulating stable pneumoperitoneum using the trocar.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein:

FIG. 2 is a perspective view of the trocar assembly of FIG. 1, showing the passive filtration cap in place on the trocar;

FIG. 3 is an exploded perspective view of the trocar assembly of FIG. 2, showing the cap removed from the trocar;

DETAILED DESCRIPTION OF THE PREFERRED EMBODIMENTS

Figure 1:
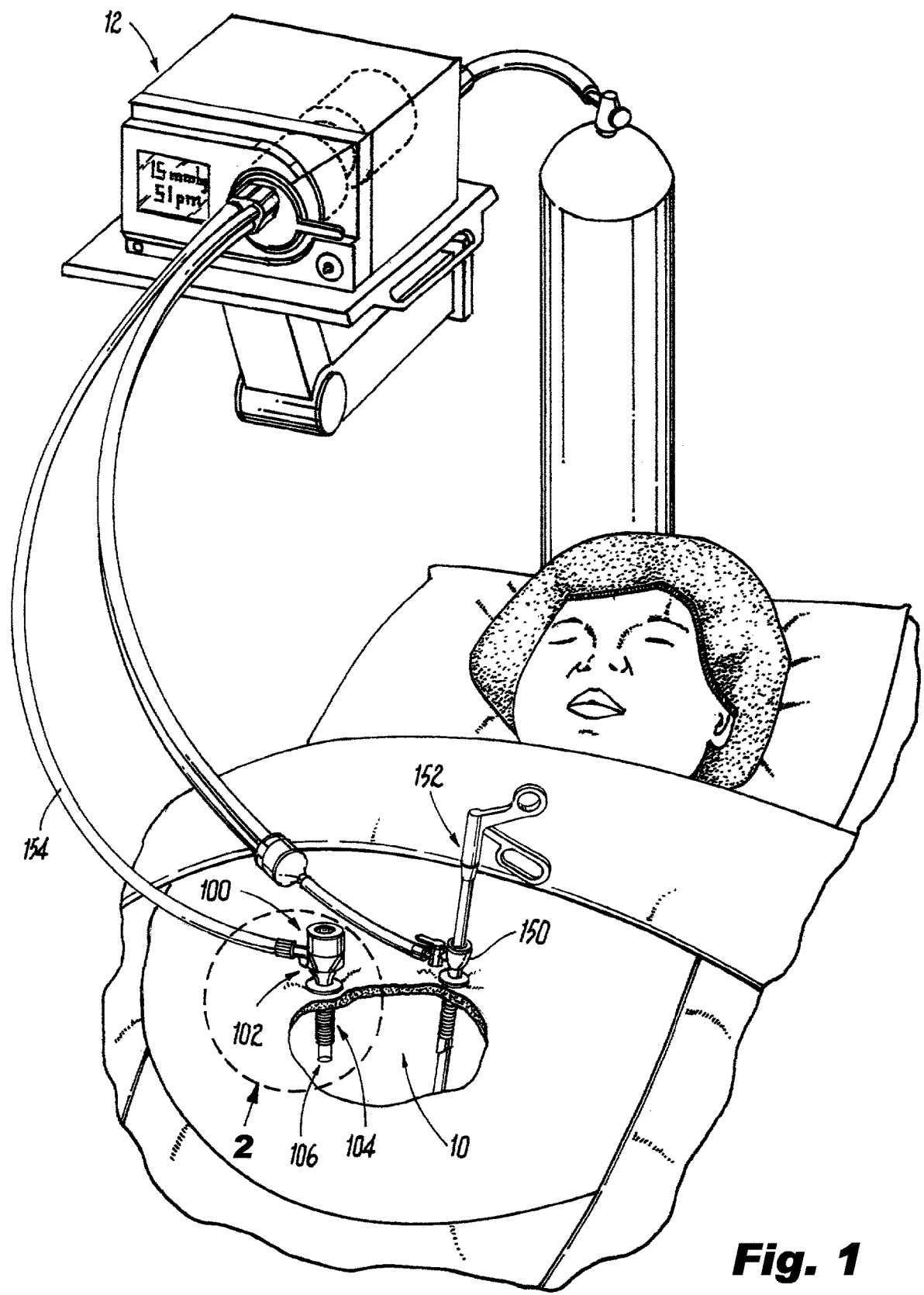
FIG. 1 is a schematic perspective view of an embodiment of a trocar assembly constructed in accordance with the present disclosure, showing the trocar assembly in situ during a procedure on a patient using insufflation.

Reference will now be made to the drawings wherein like reference numerals identify similar structural features or aspects of the subject disclosure. For purposes of explanation and illustration, and not limitation, a partial view of an embodiment of a trocar assembly in accordance with the disclosure is shown in FIG. 1 and is designated generally by reference character 100. Other embodiments of systems in accordance with the disclosure, or aspects thereof, are provided in FIGS. 2-11, as will be described. The systems and methods described herein can be used to provide passive filtration to prevent particles from within a pneumoperitoneum from entering the operating room air without impeding the performance or effectiveness of the insufflation or stable pneumoperitoneum.

The trocar assembly 100 includes a trocar 102 including an elongated tubular member 104 extending between a distal end 106 configured to be inserted into a surgical site 10, as shown in FIG. 1, and a proximal portion including a trocar housing 108 (labeled in FIG. 2). The trocar housing 108 and tubular member 104 define a main lumen 126 configured for introduction of surgical instruments into the tubular member 104, wherein the trocar housing 108 includes at least one latch receptacle 110 in the form of a ring shaped channel around the outer surface of the trocar housing 108. The trocar assembly 100 includes a cap 112, wherein a housing 114 of the cap 112 is attached to the proximal portion of the trocar 102.

With continued reference to FIGS. 2-3, the housing 114 for the cap 112 for the trocar assembly 100 can be configured to be removably attached to the proximal portion, i.e. to the trocar housing 108, of the trocar 102. The housing 114 includes a flow passage 124 therethrough, indicated by the large arrow in FIG. 5, from a distal end 116 of the housing 114 to a proximal opening 118 of the housing 114. A filter medium 120 is included within the housing 114 spanning the flow passage 124 for filtration of flow through the flow passage 124. The filter medium 120 can be an ultra-low particular air (ULPA) filter medium.

Figure 4:
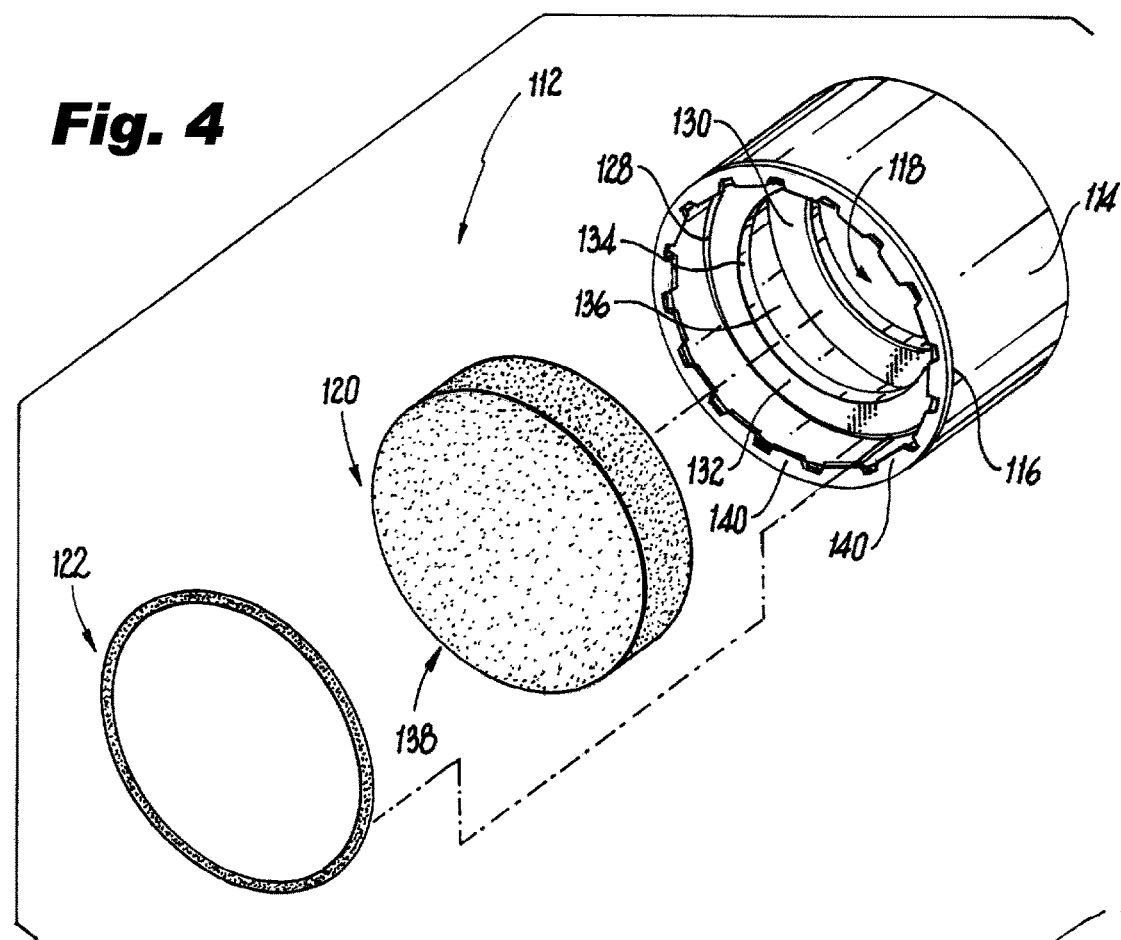
FIG. 4 is an exploded perspective view of the cap of FIG. 3, showing the filter medium and seal ring.
Figure 5:
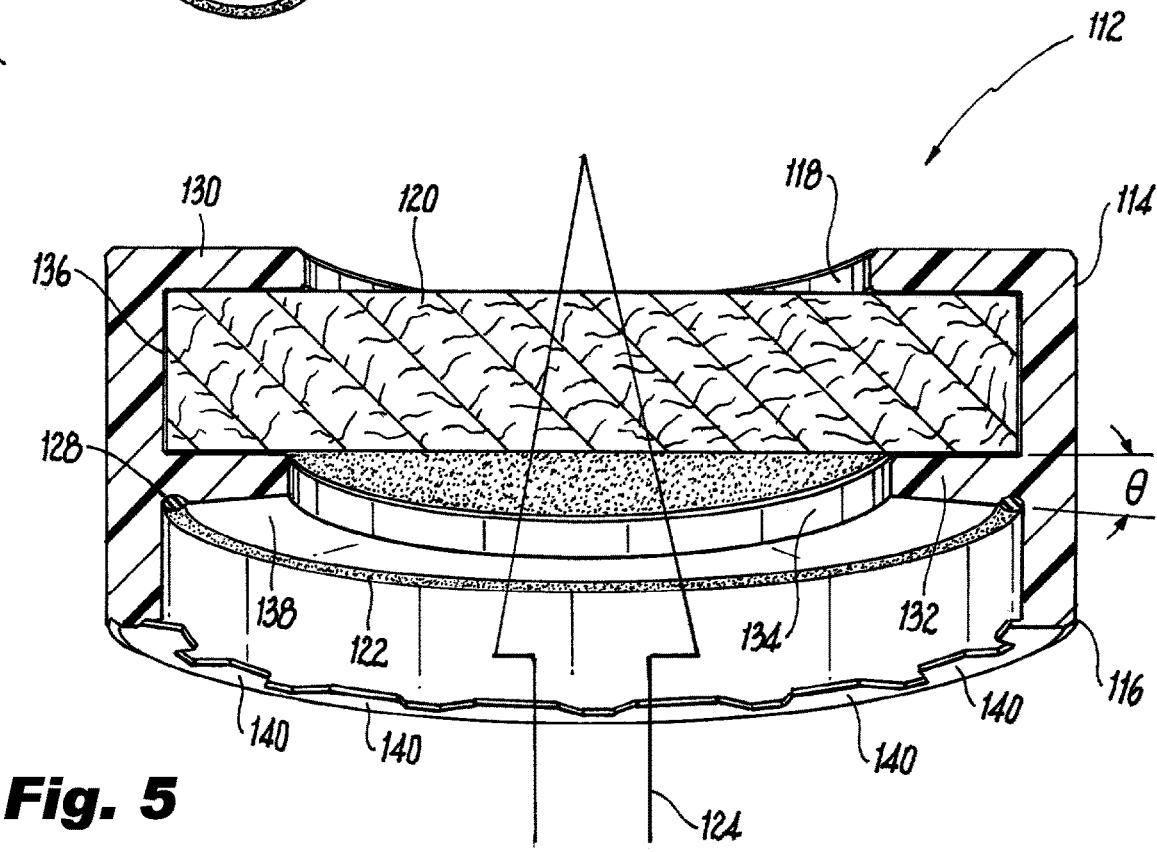
FIG. 5 is a cross-sectional perspective view of the cap of FIG. 3, showing how the filter medium is seated in the cavity of the cap housing.

With continued reference to FIGS. 4-5, a seal 122 extends circumferentially around the flow passage 124. The seal 122 is configured to engage the proximal portion, e.g trocar housing 108, of the trocar 102, to drive all flow into and out of the main lumen 126 (labeled in FIGS. 2-3) through the flow passage 124. A seal seat 128 is defined in the flow passage 124 of the housing 114. The seal 122 is seated in the seal seat 128 as shown in FIG. 5.

With continued reference to FIGS. 4-5, a first rim 130 is defined in the housing 114 about the proximal opening 118. A second rim 132 is axially spaced apart from the first rim 130 and is positioned within the flow passage 124. The second rim 132 is defined about an intermediate opening 134 of the flow passage 124. The filter medium 120 is seated in an annular cavity 136 of the housing 114 axially between the first and second rims 130, 132. In embodiments, the second rim 132 can include an adhesive layer and/or bead to secure a distal portion of the filter medium 120 in place. The filter medium 120 fills the cavity 136, and has a larger outer perimeter 138 defined in a circumferential direction than either of the proximal and intermediate openings 118, 134 so that flow through the flow passage 124 must pass through the filter medium 120. The seal seat 128 is defined in a distal side 138 of the second rim 132. The distal side 138 of the rim 132 is angled conically, as indicated by the angle θ (theta) in FIG. 5, to converge in a proximal direction, i.e. upward as oriented in FIG. 5.

The distal end 116 of the housing 114 includes a plurality of circumferentially spaced apart, inward extending latch members 140 configured to engage a respective rim or detent, i.e. of the latch receptacle 110 labeled in FIG. 3, of the trocar 102 to maintain engagement of the housing 114 to the trocar 102.

Figure 6:
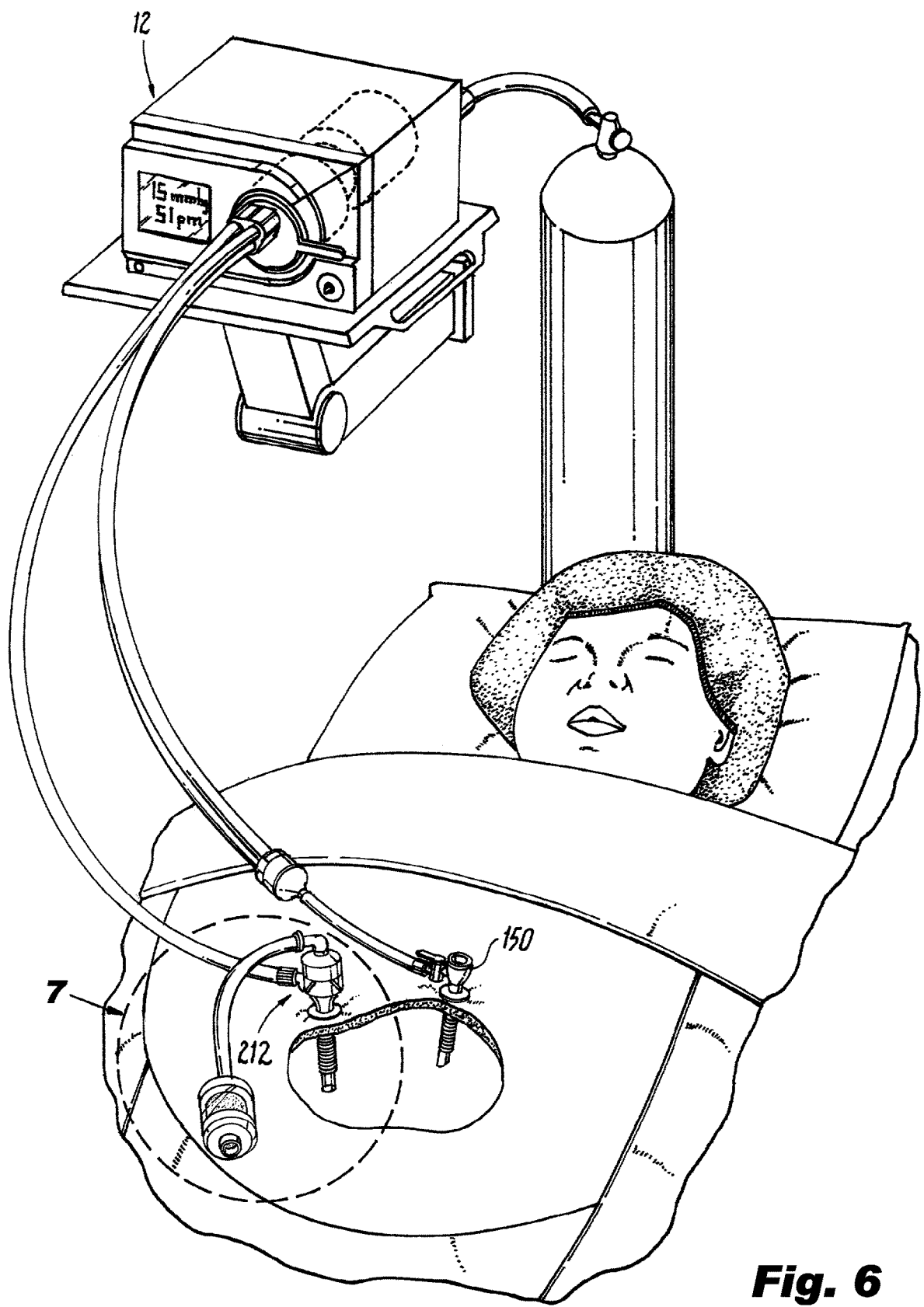
FIG. 6 is a schematic perspective view of another embodiment of a trocar assembly constructed in accordance with the present disclosure, showing the trocar assembly in situ during a procedure on a patient using insufflation.
Figure 7:
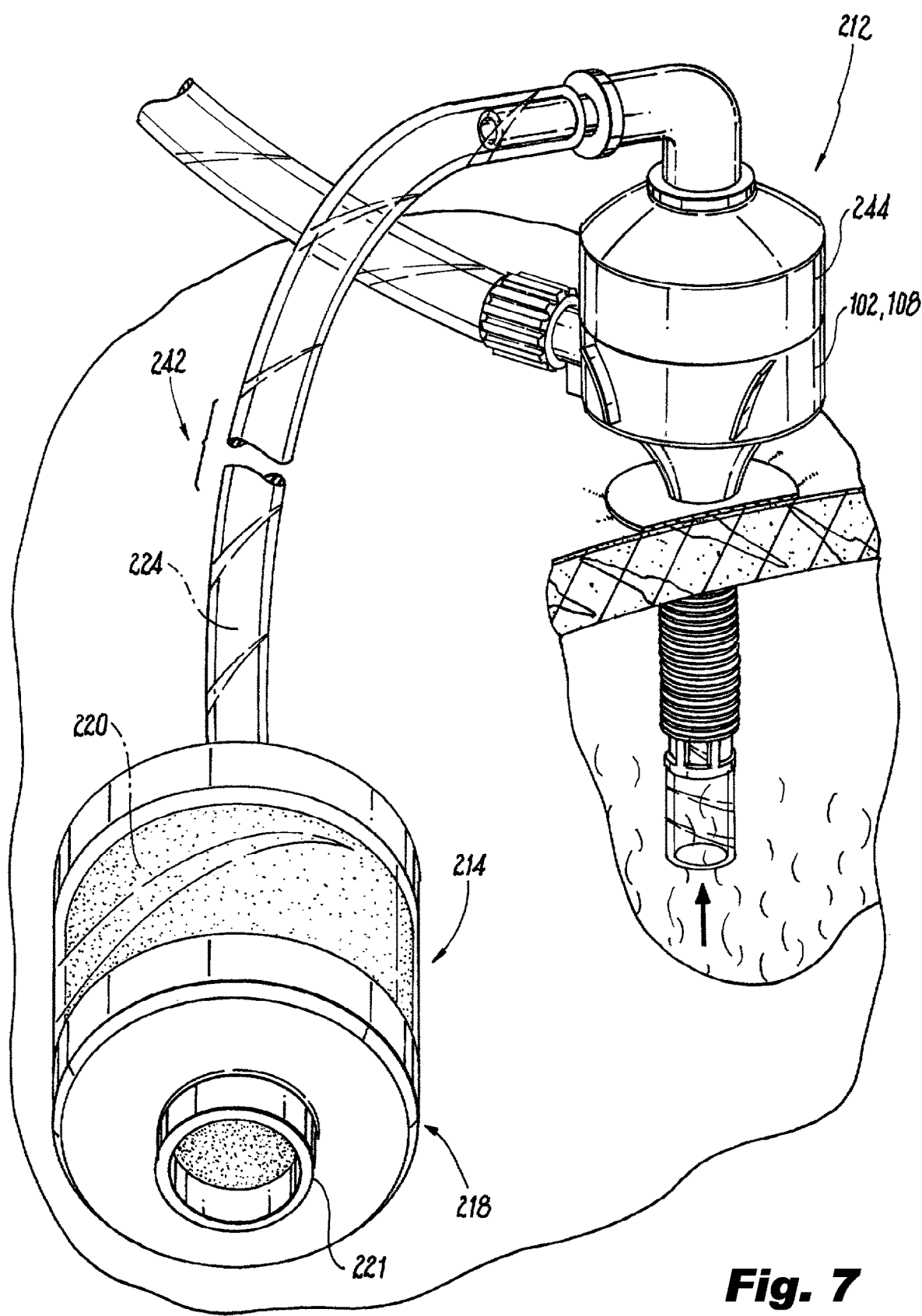
FIG. 7 is a is a perspective view of the trocar assembly of FIG. 6, showing a cap wherein the distal end of the housing of the cap includes a passive opening connected to a first end of a tube, wherein the second end of the tube is connected to an access port fitting configured to engage to the proximal portion of the trocar.
Figure 8:
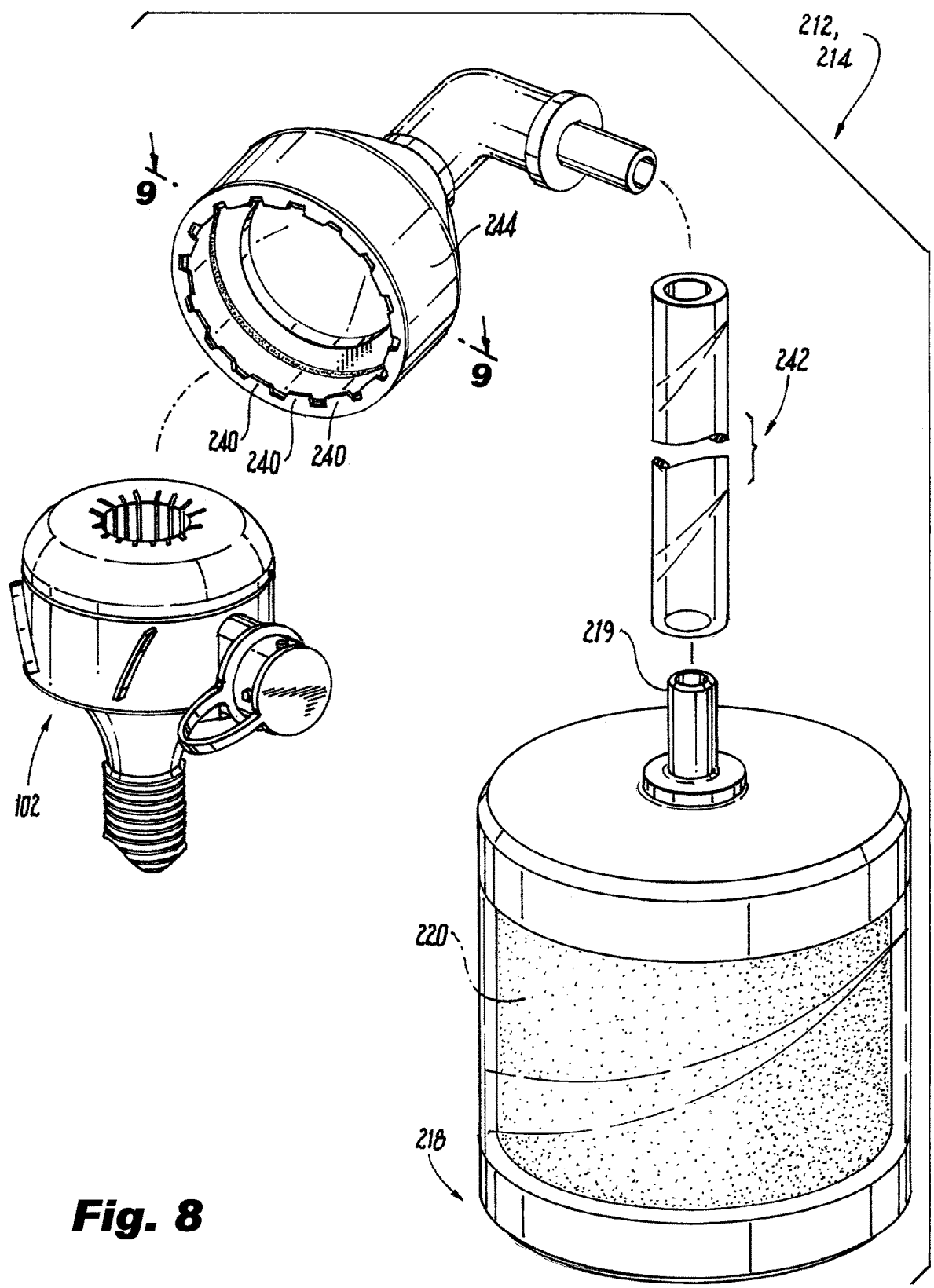
FIG. 8 is an exploded perspective view of the trocar assembly of FIG. 7, showing the cap removed from the trocar.
Figure 9:
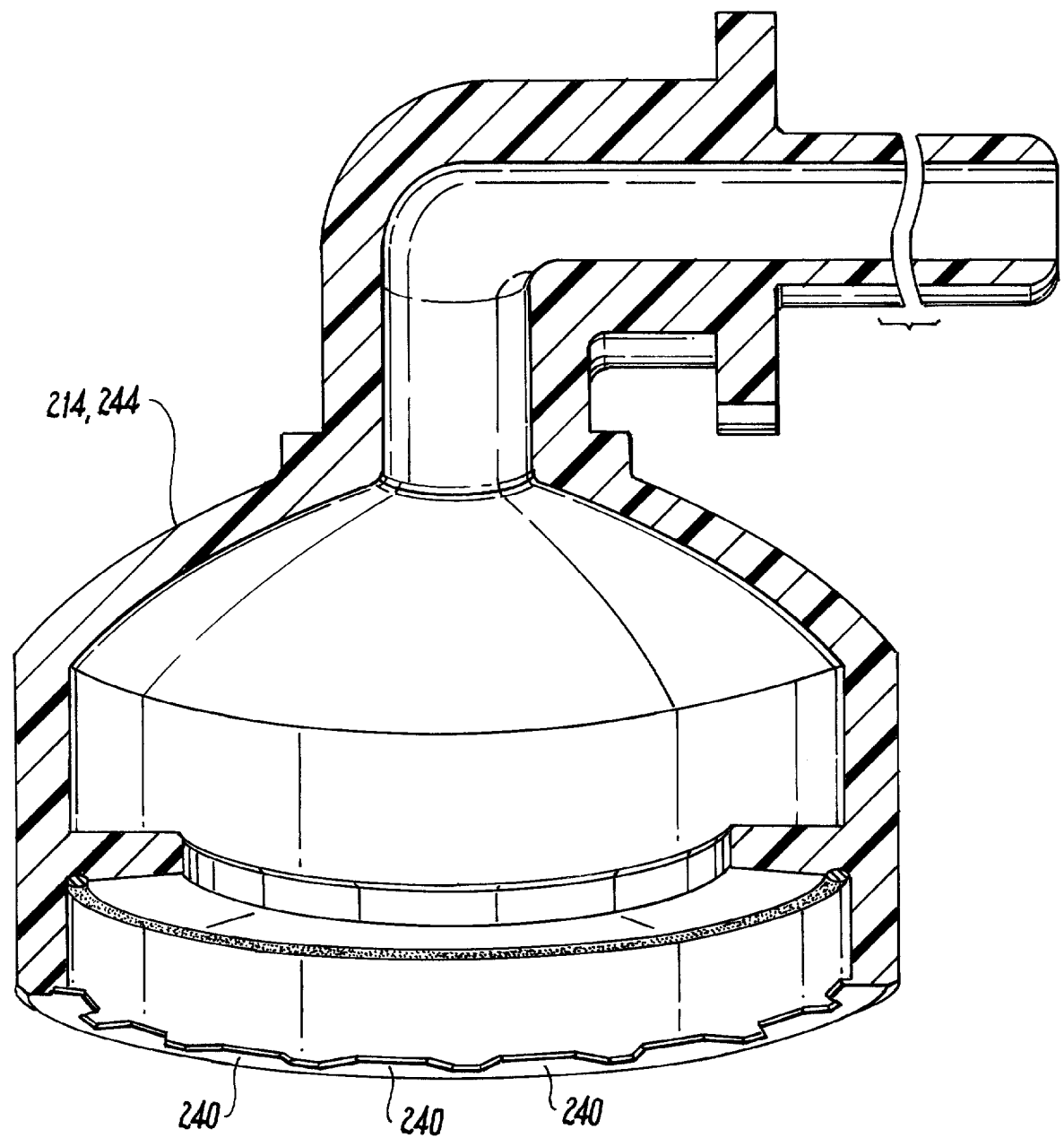
FIG. 9 is an cross-sectional perspective view of an elbow portion of the cap of FIG. 8.

Another cap 212 is shown in FIGS. 6-8. The distal end 218, shown in FIG. 8, of the housing 214 of the cap 212 includes a passive opening 219 connected to a first end of a tube 242. The second end of the tube 242 is connected to an access port fitting 244 configured to engage to the proximal portion, i.e. trocar housing 108, of the trocar 102 for passive fluid communication through the flow passage 224, tube 242, access port fitting 244, and the main lumen 126 (labeled in FIG. 2) of the trocar 102. The access port fitting 244 includes inward extending latch members 240 for removable attachment of the access port fitting 244 to the trocar 102 in the same manner as described above with reference to cap 112. The filter medium 220 in cap 212 is seated in the portion of the housing 214 between the passive opening 219 and the proximal opening 221 of the housing 214. The cap 112 and/or the cap 212 can be included with a trocar 102 in a kit.

Figure 10:
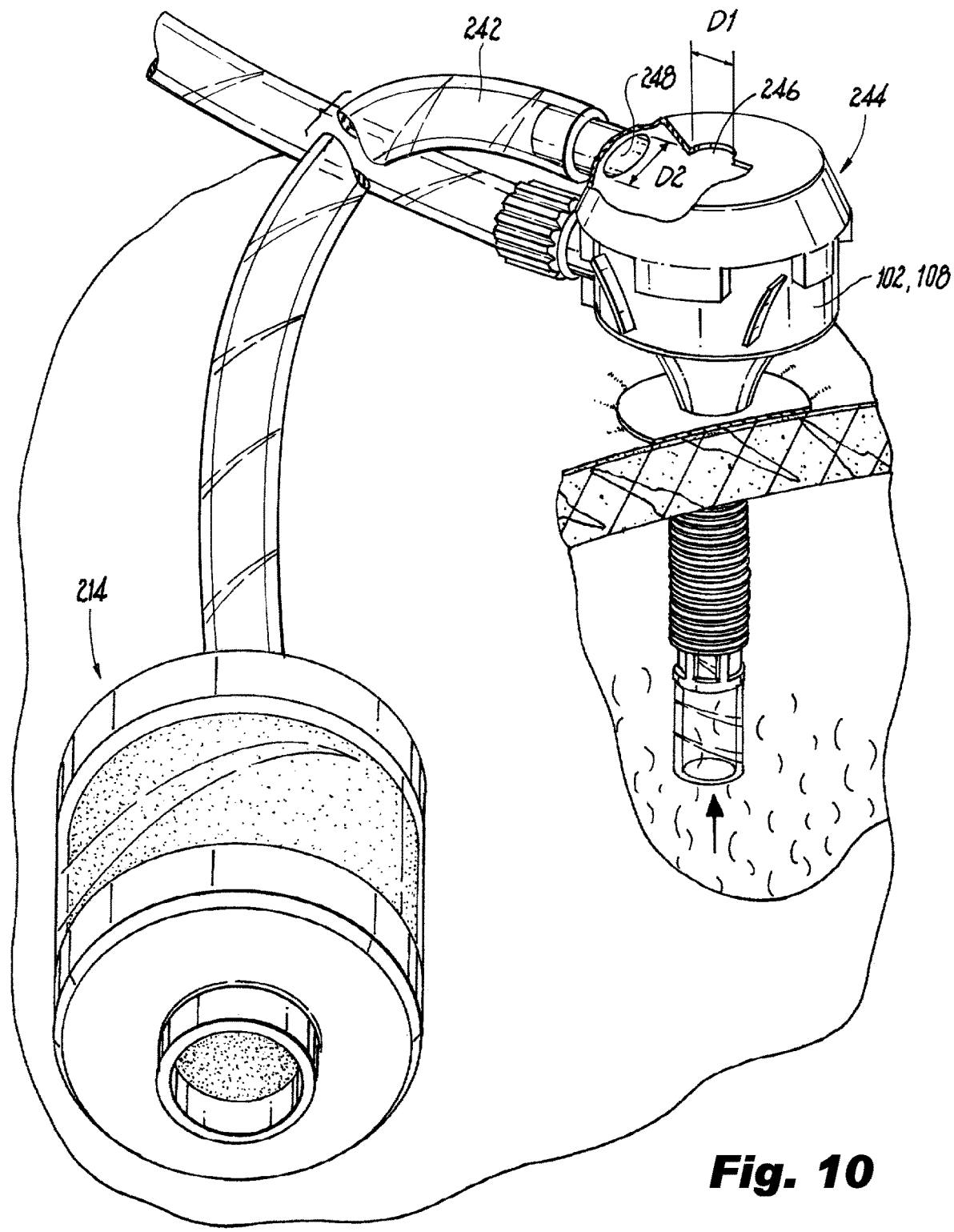
FIG. 10 is a partially cut-away perspective view of another embodiment of a cap, wherein an opening is included for passage of surgical instruments through the cap.
Figure 11:
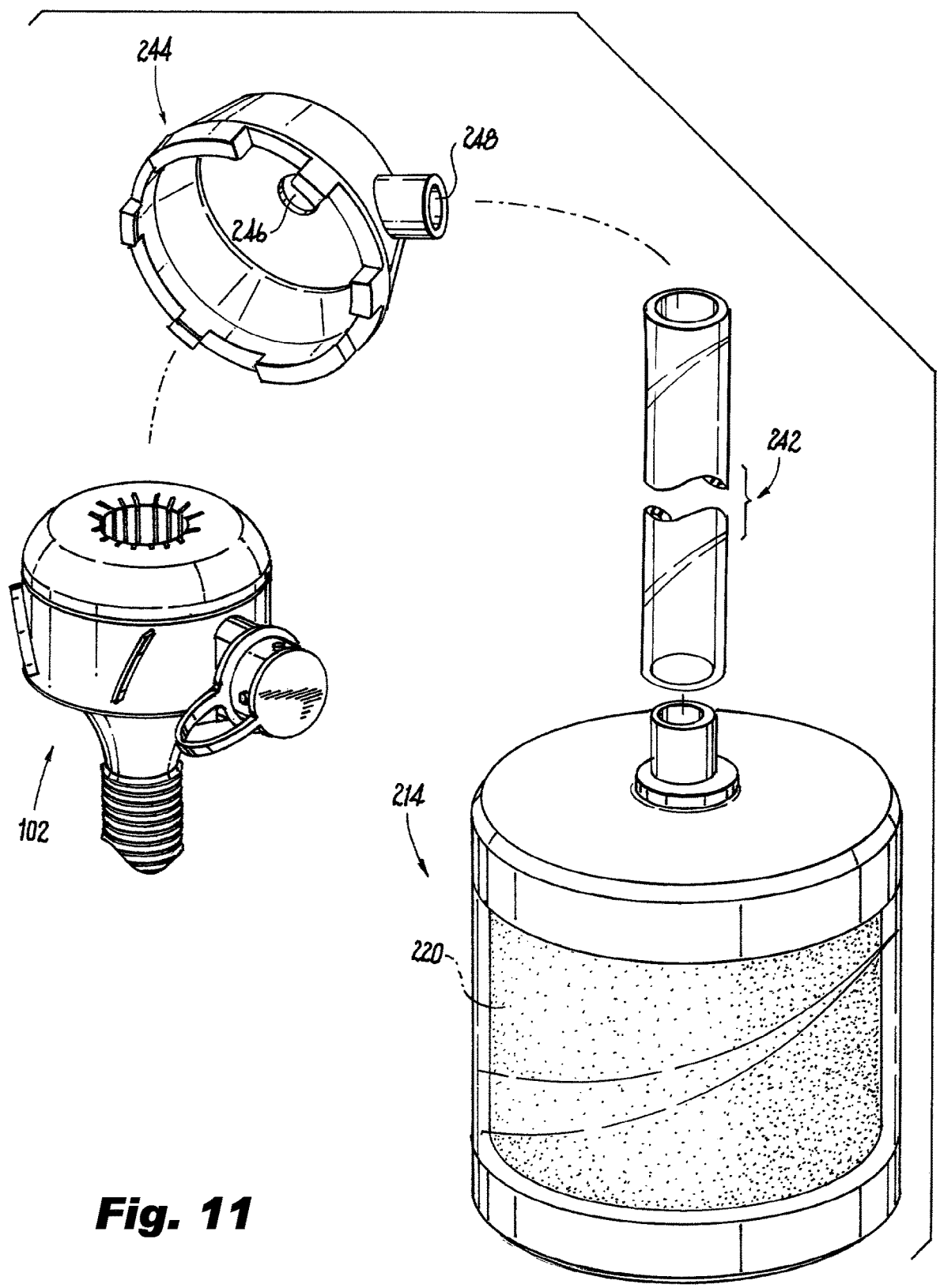
FIG. 11 is an exploded perspective view of the cap of FIG. 10, showing the trocar and filter housing.

With reference now to FIGS. 10-11, it is also contemplated that the access port fitting 244 can optionally include a first opening 246 therethrough generally aligned (e.g. relative to the longitudinal trocar axis indicated by the large arrow in FIG. 10) for passage of a surgical instrument (e.g. surgical instrument 152 of FIG. 1) therethrough and into a main lumen 126 of the trocar 102 (labeled in FIG. 1), and a second opening 248 lateral relative to the first opening 246.

The tube 242 connects to the access port fitting 244 at the second opening 248. The second opening 248 has a larger diameter D2 than the diameter D1 of first opening 246 to direct outflowing gases preferentially through the second opening 248 for filtering in the filter medium 220.

With reference again to FIGS. 1 and 6, a method includes regulating insufflation, e.g. using an insufflation system 12, of a surgical site, e.g. site 10, with a trocar, e.g. trocar 102, introduced into the surgical site and venting fluid out of the surgical site through the trocar into a space external of the surgical site, e.g. in to the operating room. The method includes capturing liquid droplets, solid particulate, and/or gas from the fluid in a filter medium, e.g. filter media 120, 220 in FIGS. 2 and 8, in a flow path, e.g. flow path 124 in FIG. 5, between the surgical site 10 and the space external of the surgical site.

The filter medium 120, 220 is external of any fluid circuit connecting between the trocar 102 and an insufflator, i.e. insufflation system 12, regulating insufflation with the trocar 102.

The method can include accessing the surgical site 10, i.e. with one or more surgical instruments 152, through second access port 150. Accessing the surgical site 10 through the second access port 150 includes accessing the surgical site 10 without accessing the surgical site 10 through the first access port, i.e. without using the trocar 102 for passage of surgical instruments 152 into the surgical site 10. It is also contemplated that the method can include accessing the surgical site through the trocar and diverting outflowing gas from the trocar though a lateral opening in a passive filtration cap on the trocar, e.g. as described above with respect to FIG. 10. The method can include evacuating smoke from the surgical site 10 through the trocar 12, e.g. through tube set 154 connecting between the trocar 102 and the insufflation system 12. The method can include regulating stable pneumoperitoneum using the trocar 102, e.g. through the tube set 154 using the insufflation system 12.

The methods and systems of the present disclosure, as described above and shown in the drawings, provide for passive filtration to prevent particles from within a pneumoperitoneum from entering the operating room air without impeding the performance or effectiveness of the insufflation or stable pneumoperitoneum. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A cap for a trocar assembly comprising:
    a housing configured to be removably attached to a proximal portion of a trocar, wherein the housing includes a flow passage therethrough from a distal end of the housing to a proximal opening of the housing;
    a filter medium within the housing spanning the flow passage for filtration of flow through the flow passage; and
    a seal extending circumferentially around the flow passage radially outward of the flow passage, wherein a first rim is defined in the housing about the proximal opening and a second rim axially spaced apart from the first rim is positioned within the flow passage, the second rim being defined about an intermediate opening of the flow passage, wherein a first rim is defined in the housing about the proximal opening and a second rim axially spaced apart from the first rim is positioned within the flow passage, the second rim being defined about an intermediate opening of the flow passage, wherein the distal side of the second rim is angled conically to converge in a proximal direction.

2. A cap for a trocar assembly comprising:
    a housing configured to be removably attached to a proximal portion of a trocar, wherein the housing includes a flow passage therethrough from a distal end of the housing to a proximal opening of the housing;
    a filter medium within the housing spanning the flow passage for filtration of flow through the flow passage; and
    a seal extending circumferentially around the flow passage radially outward of the flow passage, wherein the distal end of the housing includes at least one inward extending latch member configured to engage a respective rim or detent of the trocar to maintain engagement of the housing to the trocar.

3. The cap as recited in claim 2, wherein the seal is configured to engage the proximal portion of the trocar to drive all flow into and out of a main lumen of the trocar through the flow passage.

4. The cap as recited in claim 3, wherein a seal seat is defined in the flow passage of the housing, wherein the seal is seated in the seal seat.

5. The cap as recited in claim 2, wherein a first rim is defined in the housing about the proximal opening and a second rim axially spaced apart from the first rim is positioned within the flow passage, the second rim being defined about an intermediate opening of the flow passage.

6. The cap as recited in claim 5, wherein the filter medium is seated in a cavity of the housing axially between the first and second rims.

7. The cap as recited in claim 6, wherein the filter medium has a larger outer perimeter defined in a circumferential direction than either of the proximal and intermediate openings so that flow through the flow passage must pass through the filter medium.

8. The cap as recited in claim 6, wherein the filter medium fills the cavity.

9. The cap as recited in claim 5, wherein a seal seat is defined in the flow passage of the housing, in a distal side of the second rim, wherein the seal is seated in the seal seat.

10. The cap as recited in claim 2, wherein the distal end of the housing includes a plurality of circumferentially spaced apart, inward extending latch members configured to engage a respective rim or detent of the trocar to maintain engagement of the housing to the trocar.

11. The cap as recited in claim 2, wherein the filter medium is an ultra-low particulate air (ULPA) filter medium.

12. A cap for a trocar assembly comprising:
a housing configured to be removably attached to a proximal portion of a trocar, wherein the housing includes a flow passage therethrough from a distal end of the housing to a proximal opening of the housing;
a filter medium within the housing spanning the flow passage for filtration of flow through the flow passage, wherein the distal end of the housing includes a passive opening connected to a first end of a tube, wherein a second end of the tube is connected to an access port fitting configured to engage to the proximal portion of the trocar for passive fluid communication through the flow passage, tube, access port fitting, and trocar wherein the access port fitting defines a first opening therethrough generally aligned for passage of a surgical instrument therethrough and into a main lumen of the trocar, and a second opening lateral relative to the first opening, wherein the tube connects to the access port fitting at the second opening.

13. The cap as recited in claim 12, wherein the second opening is larger than the first opening to direct outflowing gases preferentially through the second opening for filtering in the filter medium.

14. A trocar assembly comprising:
a trocar including an elongated tubular member extending between a distal end configured to be inserted into a surgical site and a proximal portion including a trocar housing configured for introduction of surgical instruments into the tubular member, wherein the trocar housing includes at least one latch receptacle; and
a cap including:
a housing of the cap attached to the proximal portion of a trocar, wherein the housing of the cap includes a flow passage therethrough from a distal end of the housing of the cap to a proximal opening of the housing of the cap;
a filter medium within the housing of the cap spanning the flow passage for filtration of flow through the flow passage; and
a seal extending circumferentially around the flow passage radially outward of the flow passage.

15. A kit comprising:
a trocar including an elongated tubular member extending between a distal end configured to be inserted into a surgical site and a proximal portion including a trocar housing configured for introduction of surgical instruments into the tubular member, wherein the trocar housing includes at least one latch receptacle; and
a cap including:
a housing of the cap configured to be removably attached to the proximal portion of the trocar, wherein the housing of the cap includes a flow passage therethrough from a distal end of the housing of the cap to a proximal opening of the housing of the cap; and
a filter medium within the housing of the cap spanning the flow passage for filtration of flow through the flow passage; and
a seal extending circumferentially around the flow passage radially outward of the flow passage.

* * * * *